US006659962B2

United States Patent

Ricciardelli

(10) Patent No.: US 6,659,962 B2
(45) Date of Patent: Dec. 9, 2003

(54) RESPIRATORY MEASUREMENT SYSTEM WITH CONTINUOUS AIR PURGE

(75) Inventor: Robert H. Ricciardelli, Waukesha, WI (US)

(73) Assignee: CardioPulmonary Technologies, Inc., Pewaukee, WI (US)

( * ) Notice: Subject to any disclaimer, the term of this patent is extended or adjusted under 35 U.S.C. 154(b) by 0 days.

(21) Appl. No.: 10/099,633

(22) Filed: Mar. 15, 2002

(65) Prior Publication Data

US 2002/0103444 A1 Aug. 1, 2002

Related U.S. Application Data

(60) Division of application No. 09/545,704, filed on Apr. 7, 2000, now Pat. No. 6,358,215, which is a division of application No. 09/310,561, filed on May 12, 1999, now Pat. No. 6,089,105, which is a division of application No. 09/172,486, filed on Oct. 14, 1998, now Pat. No. 5,925,831, which is a continuation-in-part of application No. 08/953,868, filed on Oct. 18, 1997, now abandoned.

(51) Int. Cl.[7] ................................................. A61B 5/08
(52) U.S. Cl. ...................................... 600/538; 600/533
(58) Field of Search ............................... 600/529, 532, 600/533, 538; 128/200.24, 204.18

(56) References Cited

U.S. PATENT DOCUMENTS

| 4,274,425 A | 6/1981 | Lutz et al. |
| 4,382,806 A | 5/1983 | Hakala et al. |
| 4,592,368 A | 6/1986 | Ricciardelli et al. |
| 4,713,095 A | 12/1987 | Ricciardelli |
| 4,993,269 A | 2/1991 | Guillaume et al. |
| 5,088,332 A | 2/1992 | Meriläinen et al. |
| 5,347,843 A | * 9/1994 | Orr et al. ..................... 73/1.34 |
| 5,676,131 A | 10/1997 | Anderson et al. |

* cited by examiner

Primary Examiner—Max F. Hindenburg
Assistant Examiner—Navin Natnithadha
(74) Attorney, Agent, or Firm—Boyle Fredrickson Newholm Stein & Gratz S.C.

(57) ABSTRACT

In a respiratory air flow measuring monitor, a subassembly for analyzing certain respiratory gases through infrared spectroscopy includes an infrared emitter and an infrared detector, the amount of energy detected by the detector corresponding to the concentration of the gas selected for analysis. The subassembly includes a gas sample chamber that utilizes an elliptical reflecting surface for the infrared light source. The light source and detector are both oriented longitudinally along the axis of the ellipse and the light source and detector are each located at the two focal points of the ellipse in order to optimize the light absorption reading. The gas content analyzer subassembly additionally incorporates various compensatory features, allowing for automatic temperature and pressure compensation. Specifically, the analyzer includes a continuous air puree feature that inhibits moisture from collecting within the lumen tubes of the analyzer and interfering with the operation of the analyzer.

20 Claims, 10 Drawing Sheets

RESPIRATORY MEASUREMENT SYSTEM WITH CONTINUOUS AIR PURGE

RELATED APPLICATIONS

The present application is a divisional of application Ser. No. 09/545,704 filed on Apr. 7, 2000 now U.S. Pat. No. 6,358,215, which is a divisional of application Ser. No. 09/310,561 filed on May 12, 1999 now U.S. Pat. No. 6,089,105, which is a divisional of application Ser. No. 09/172,486 filed on Oct. 14, 1998 now U.S. Pat. No. 5,925,831, is a continuation-in-part of application Ser. No. 08/953,868 filed on Oct. 18, 1997, now abandoned.

BACKGROUND OF THE INVENTION

1. Field of the Invention

The present invention relates to a respiratory measurement system. The primary components of the system include a respiratory air flow sensor, a microprocessor based module, lumen tubing for connecting the respiratory air flow sensor to the module, a connector for connecting the lumen tubing to the module, a mechanism for optionally purging the system, and a mechanism for optionally measuring content of a particular respiratory gas. This application specifically concerns an apparatus for analyzing the content of a specified respiratory gas, such as carbon dioxide ($CO_2$) and nitrous oxide ($N_2O$), using infrared spectroscopy.

2. Background of the Related Art

A patient receiving anesthesia or in intensive care, for example, needs to have his or her inhalations and exhalations continuously monitored. Respiratory mechanics refers to the monitoring of the physical parameters of a mechanically ventilated patient's airway. The parameters include airway flow and pressure. Various measuring devices are used to measure the air flow rate. For some patients the content of particular respiratory gases flowing from or to the lungs must also be analyzed.

For measuring the air flow rate, it has been well known to use a tubular device which measures the pressure differential across a portion of the tube. An example of such a device is described in U.S. Pat. Nos. 5,535,633 and 5,379,650 (referred to hereafter collectively as "the '633 device"). The '633 device depends on the creation of a direct impedance to the axial gas flow through the tube in order to obtain the pressure differential from which the air flow rate can be derived by the application of a certain nonlinear mathematical formula. The tube is formed from plastic and has an internal diameter or radius which is partially blocked by a strut which obstructs the center of the air passage. Such devices are classified as a fixed orifice air flow sensor because the internal geometry of the device is in fact fixed. Current fixed orifice air flow sensors including the '633 device, however, present problems which arise from turbulence in the air flow through the sensor which causes a nonlinear response of pressure change versus air flow rate through the device. To account for the nonlinear response, the '633 system includes additional hardware which gain stages the pressure readings. Current fixed orifice devices such as the '633 device also add a relatively high amount of resistance to the airway, which adds work to the patient just to breathe.

Other known air flow measuring devices rely on a variable area obstruction of the patient's respiratory air passageway. Such devices are also tubular members which measure the pressure differential of the air flow through the tube. An example of a variable area obstruction air flow meter is described in U.S. Pat. No. 5,038,621 (referred to hereafter as "the '621 device"). The obstruction in the '621 air flow meter is comprised of a flexible elastic membrane which extends into the flow stream. A portion of the membrane deflects as the air flows through the obstruction. Variable obstruction air flow sensors normally produce a more linear pressure change versus flow rate measurement than do the current fixed orifice-type sensors, but a variable obstruction sensor also adds a relatively high amount of resistance to the air flow. Variable obstruction air flow sensors are also considerably more expensive to manufacture than are the fixed orifice type. The thin membrane in particular is difficult to manufacture to consistently tight specifications, so there is a significant amount of variability from one part to the other. The '621 device is also made from multiple components, which of course require assembly that naturally adds to the cost of the device.

To obtain an accurate pressure differential measurement, a great amount of resistance by the obstruction in the air flow sensor is desired. This must, however, be balanced with the fact that a high resistance adds work to the patient just to breathe, which is, of course, a reason to keep the amount of resistance low. The internal geometry of the air flow sensor should also be of a type which provides the most accurate measurement possible over a range of air flow rates. Ideally a sensor exhibiting a linear or nearly linear pressure changes versus flow rate curve through the full range of anticipated respiratory pressures and flow rates is desired.

A further feature of a respiratory measurement system is the connector that is used to attach the air flow sensor to the microprocessor based analyzer module. In known prior art systems the connector for connecting the air flow sensor has been normally comprised of a first molded receptacle which is releasably connectable to a second molded receptacle, i.e., matching male and female receptacles. A typical example of such a device is the modular constructed connector disclosed in U.S. Pat. No. 5,197,895 (referred to hereafter as "the '895 device"). The '895 device and other similarly designed male/female-type connectors are normally quite expensive to treat as throw away or disposable devices. An improved connector for connecting the air flow sensor to the analyzer module, especially one which provides all of the necessary functions required of a connector for a respiratory system of the type presented here yet reduces or eliminates the number of components and thus reduces cost, is therefore desired.

Another feature of a respiratory measurement system is a means for purging the system of condensation or other debris that may block the airways or block the lumen tubing which attaches the air flow sensor to the analyzer module. In a patient ventilator circuit, natural cooling of the respiratory gases causes condensation of water vapor in the air tubes. If left undrained or unattended, the moisture will pool and may clog the tubing connected to the air flow sensor. A ventilator works by periodically compressing a volume of air which of course increases the air pressure in the ventilator circuit in order to force air into the patient's lungs. The air is then returned to atmospheric pressures which allows the patient to exhale. This continuously fluctuating pressure in the breathing passage causes condensation in the ventilator circuit to migrate into the lumen tubes that are used for measuring the pressure differential in the air flow sensor mentioned above. Of course, a blockage in the lumen tubes will cause errors in the air flow measurement. In most known prior art systems, the lumen tubes are periodically purged with a short burst of air to clear any condensation or other obstruction that may be blocking the airway. One disadvantage of this method is that no measurements can be taken during the purge. Additionally, the purges normally occur at timed intervals, e.g., five minutes. In the event that a blockage occurs only one minute into the period, the air flow measurements will be incorrect for the remainder of the period. It is also difficult at times to determine whether a blockage has actually occurred because in some instances the signal may appear like an actual breath. An improved method of purging the pressure measuring airway passages in a respiratory air flow sensor is therefore desired.

In a respiratory measurement system it is also desirable to periodically measure the content of particular respiratory gases. There are many types of gas analysis procedures, but one commonly used method is infrared spectroscopy. In infrared spectroscopy, a sample of the gas extracted from the patient's respirations is passed through a gas chamber located between an IR emitter and an IR detector. Particular gases, such as carbon dioxide ($CO_2$) or nitrous oxide ($N_2O$) are known to absorb particular wavelengths of light. The presence and concentration level of such a gas can therefore be determined by measuring the amount of light at the selected wavelength that has been absorbed by the gas sample. Known IR analyzers are prone to consuming more energy than is really necessary and inaccuracies due to unsatisfactory arrangement of the emitter and detector. An improved IR gas analyzer that better utilizes and focuses the infrared light energy is therefore desired. Known IR analyzers are also prone to failure after a short period of use, and so a compactly designed field replaceable IR analyzer module is also desired.

SUMMARY OF THE INVENTION

A respiratory measurement system is presented. The system is comprised of a respiratory air flow sensor, a microprocessor based analyzer module, a set of lumen tubes for connecting the air flow sensor to the module, a connector for connecting the lumen tubing to the module, an electronic subassembly for calculating the respiratory air flow rate based on pressure differential measurements received from the air flow sensor, an infrared emitter and detector subassembly for analyzing the gaseous content of specified respiratory gases of a patient, and a pneumatic subassembly for purging the system with a continuous low pressure and low volume air flow.

The system includes three airway passages in communication with the patient's ventilated respiratory airway that is being monitored. Two of the airway passages are used to measure two airway pressures values for computing certain respiratory parameters. These parameters include inspired and expired respiratory air flow, pressure and volume. The third airway passage is used for extracting samples of the patient's exhalations for analysis.

The air flow sensor is designed for placement into the ventilator circuit between the patient's endotracheal tube and the ventilator. The airflow sensor is comprised of a tubular member providing a passage for the flow of air between the patient's airway and the ventilator. The air flow sensor is a fixed orifice type sensor having a specified internal geometry which creates a resistance to the patient's respirations.

The internal geometry of the air flow sensor is defined by the cylindrical walls of the tubular housing, and by a plurality of elongated aerodynamically curved vanes which extend from the internal surface to the cylindrical walls of the tubular member inwardly into the air passage. The internal geometry of the vanes creates a measurable pressure drop as air flows through the sensor. The unique internal geometry for a flow sensor as presented herein produces a resistance to the air flow which is far less turbulent than in current known fixed orifice sensors. The laminarization of the flow produces a nearly linear pressure versus flow rate response curve which greatly aids in the calculation of the patient's respiratory air flow rates. In the present invention, the air flow rate is calibrated by measuring the pressure differential between two longitudinally spaced apart pressure measuring air ports within the air flow sensor. The sensor also includes a third air port for extracting a gas sample from the air flow for analysis.

The system further includes lumen tubing for connecting the air flow sensor to the analyzer module, and a novel connector for connecting the lumen tubing to the module. The lumen tubing is comprised of three tubes, two for transmitting the pressure signals and the third for transmitting the gas sample from the air flow sensor to the analyzer module. One of the tubes has an outer diameter which differs from the outer diameters of the other two tubes to ensure that the air flow sensor and analyzer module are connected together with the proper polarity with respect to the pressure changes being monitored.

The novel connector presented herein is comprised of a single molded housing specially designed to directly receive the triple lumen tubing. The tubing requires no special machining or preparation, the connector is instead capable of accepting just the raw square cut ends of the tubing, and accepts the tubing only if it is attached to the connector at the proper polarity. The matching male/female receptacles commonly found in the prior art are therefore unnecessary. The connector also includes a means for determining a positive connection of the lumen tubing to the connector, and a means for identifying the particular type of air flow sensor being used. In this regard the connector is comprised of two pairs of internal LED emitters and detectors strategically located around the periphery of the connector housing. The emitters and detectors are oriented such that when the clear plastic tubing is correctly placed into a socket in the connector housing, light energy from the emitters is refracted by the tubing and thereby directed to impinge onto the detector. The first emitter and detector combination is used to determine the presence of the lumen tubing. When the tubing is not present or not properly seated, the first detector remains dark and the analyzer inactive. The second emitter and detector combination is used for identification of the particular air flow sensing device in use.

The system further includes a pneumatic subassembly for purging the tubes and air sensor. The system places a very low, continuous flow of gas into the lumen tubing. A low flow continuous purge reduces the depth that compressed gas from the ventilator enters into the lumen tubing, and also inhibits water droplets from forming near the air port openings for the lumen tubing in the air flow sensor. A continuous purge therefore prevents obstructions from forming in the lumen tubing in the first instance.

The two lumen tubes used for measuring the pressure differential in the air flow sensor are both subjected to substantially the same continuous low pressure air flow. Because the air flows being introduced by the two lines being purged are of the same pressure, the two added pressure values effectively offset each other so that the measured pressure difference in the ventilator circuit being monitored remains unaffected. This approach also permits continuous monitoring without the interruptions encountered in the periodic purge systems of the prior art. A continuous purge also employs less hardware, eliminates certain valves necessarily required in a periodic purge system and therefore significantly reduces the cost of the system.

The system further includes a subassembly for analyzing certain respiratory gases through infrared spectroscopy. Molecules of diatomic gases, such as carbon dioxide ($CO_2$) and nitrous oxide ($N_2O$) absorb a specific wavelength of light energy. If one passes $CO_2$ or $N_2O$ between an infrared emitter and an infrared detector, the amount of energy detected by the detector corresponds directly to the concentration of the gas of choice. The present invention includes a low power infrared $CO_2$ or $N_2O$ sensor that has a small physical size, has a very short warm-up time, efficiently dissipates heat generated by the light source, and therefore optimizes the battery life. The IR sensor further includes a gas sample chamber which effectively utilizes an elliptical reflecting surface for the infrared light source. The light source and detector are both oriented longitudinally along the axis of the ellipse and the light source and detector are each located at the two focal points of the ellipse in order to optimize the light absorption reading.

The gas content analyzer additionally incorporates various compensatory features, allowing for automatic temperature and pressure compensation. For ease of use and serviceability, the present invention includes a field replaceable IR sensor subassembly which includes electronic memory chips for calibrating temperature and pressure constants used in respiratory measurements.

Accordingly, the primary objects of the present invention are to provide a respiratory measurement system which overcomes the problems of the prior art by providing an air flow sensor device having an internal geometry which optimizes the process for measuring the air flow rate and gas content of a patients respirations; to provide a novel connector for connecting lumen tubing from the air flow sensor directly to a gas analyzer module; to provide within the module an electronic subassembly for analyzing and calculating the air flow rate of respiratory gases; to provide in the analyzer module an infrared emitter and infrared detector subassembly for measuring the content of certain respiratory gases; to provide a means for continuously purging a respiratory measurement system with a low volume air flow; and to provide a system which includes disposable or replaceable components which are highly cost effective in their design and manufacture.

Other objects and advantages of the invention will become apparent from the following description which sets forth, by way of illustration and example, certain preferred embodiments of the invention.

BRIEF DESCRIPTION OF THE DRAWINGS

The drawings, which constitute a part of the specification and include exemplary embodiments of the present invention, include the following.

DETAILED DESCRIPTION OF THE PREFERRED EMBODIMENT

Figure 1:
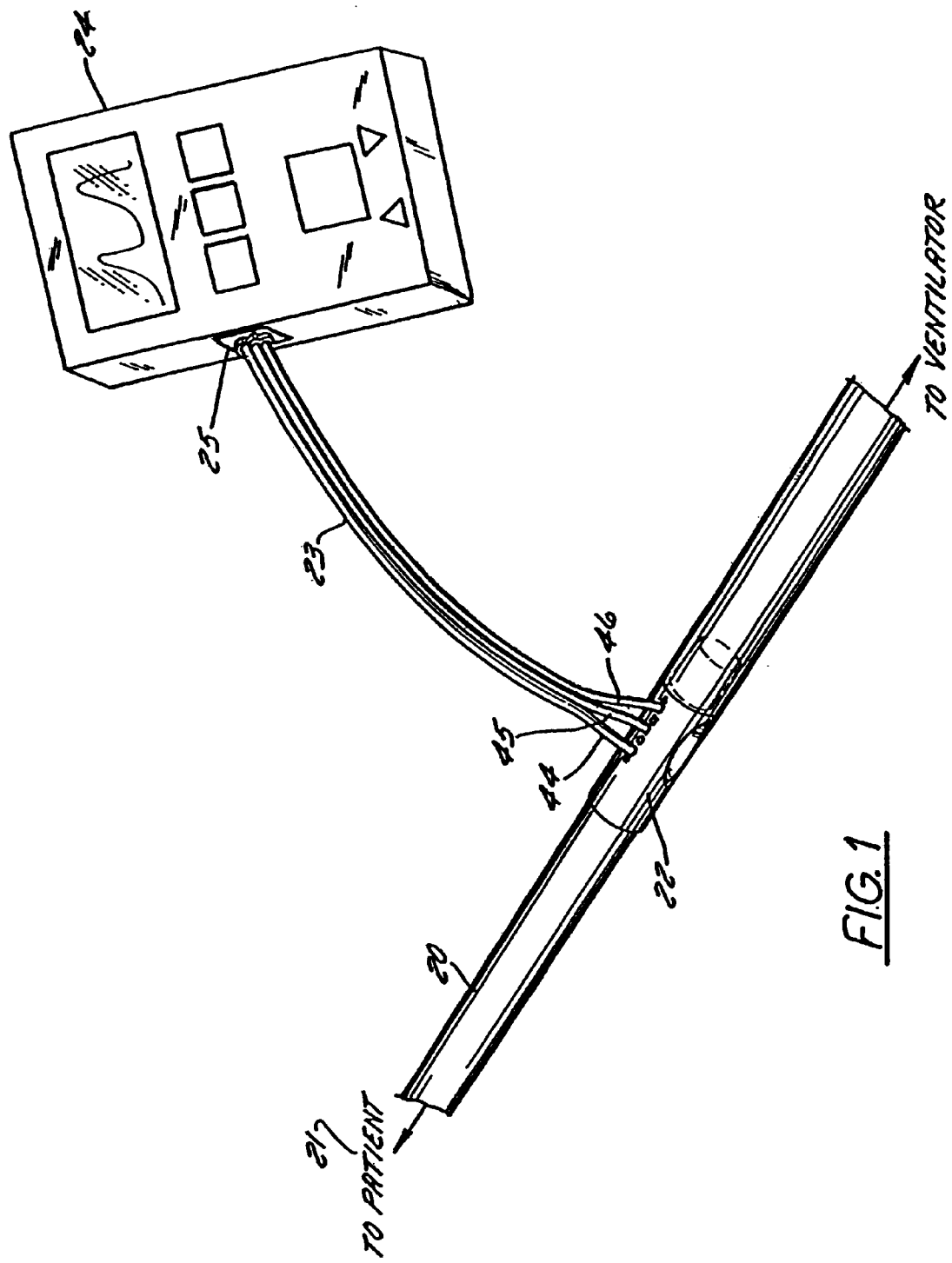
FIG. 1 is a plan view of the respiratory measurement system of the present invention.
Figure 2A:
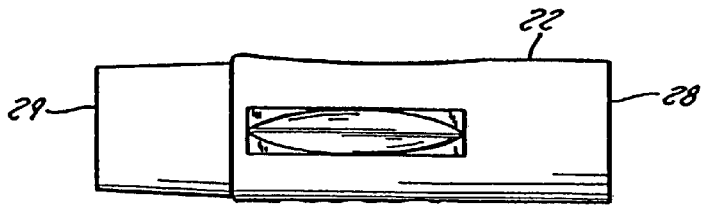
FIGS. 2A, B, C, D, E, and F are top, front, bottom, rear, left side and right side views, respectively, of the air flow sensor of the present invention.
Figures 2B, 2E, 2F:
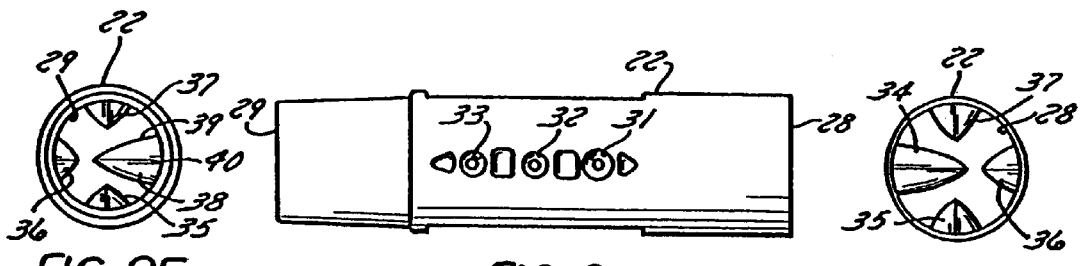
Figure 2C:
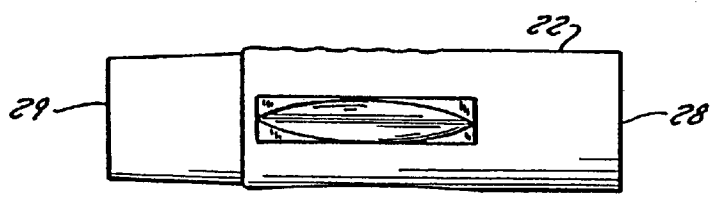
Figure 2D:
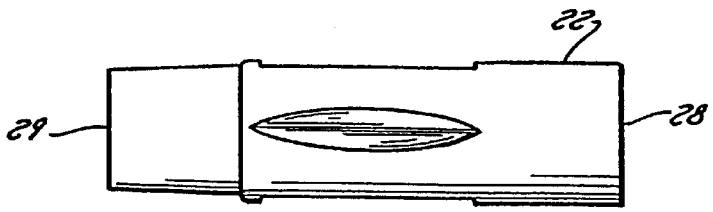
Figure 3:
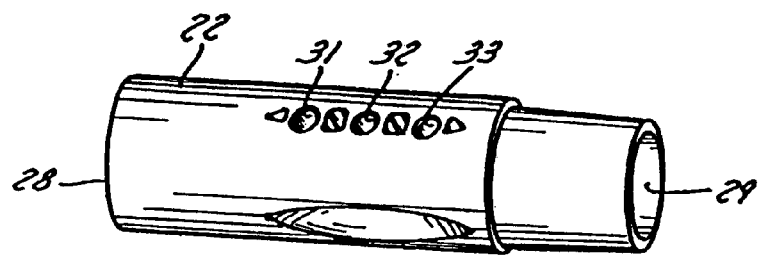
FIG. 3 is a perspective view of the air flow sensor.
Figure 4:
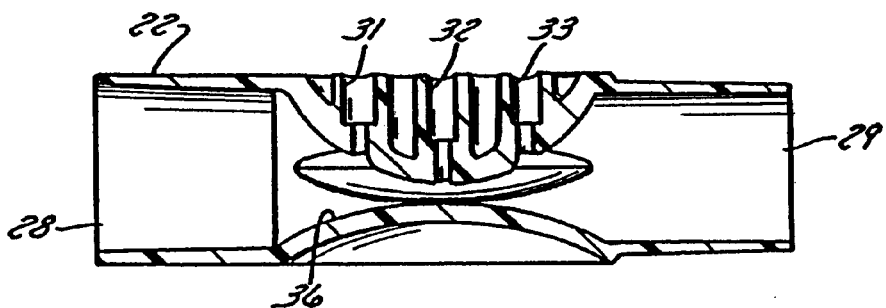
FIG. 4 is a cross-section view of the air flow sensor.
Figure 5:
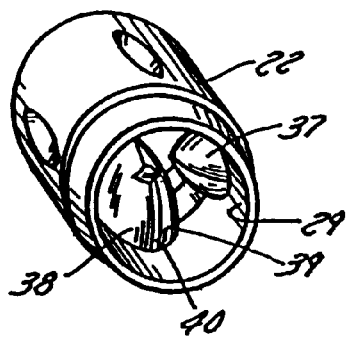
FIGS. 5 and 6 are perspective view of the open ends of the air flow sensor.
Figure 6:
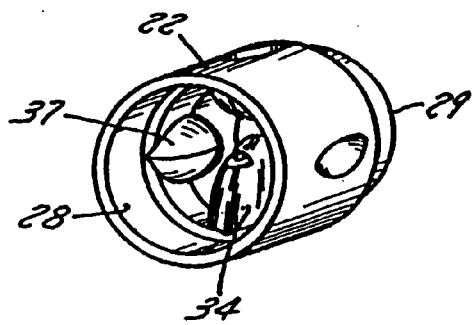

Referring to the drawings and in particular to FIG. 1, a ventilator (not shown) provides a source of air through a tube 20 to a patient 21. Patients connected to mechanical ventilators require an artificial airway placed in the nasal or oral endotracheal tube (referred to as intubation), or a tracheotomy tube placed directly into the trachea through a surgical opening in the neck.

A system for monitoring and measuring the patient's respirations is comprised of an air flow sensor 22 for measuring the pressure differential of the air flowing through the ventilator circuit and for extracting gas samples for analysis, lumen tubing 23 for connecting the air flow sensor to a microprocessor based analyzer module 24, and a connector 25 attached to the module housing for selectively connecting and disconnecting the lumen tubing to the analyzer module. Within the analyzer module are, among other elements, an electronic subassembly for calculating the air flow rate based on pressure differential signals received from the air flow sensor 22, an infrared analyzer subassembly 26 for analyzing the content of particular respiratory gases extracted from the patient's respirations, and a pneumatic subassembly 27 for continuously purging the lumen tubing 23.

1. Air Flow Sensor

Referring to FIGS. 1–6, the air flow sensor 22 consists of a substantially hollow, generally cylindrical tubular member. The sensor is preferably fabricated from a common medical grade of polycarbonate plastic, which is quite inexpensive so that the air flow sensor 22 may be disposed of after use by a single patient. The air flow sensor 22 has a first open end 28 which leads to the patient 21 and a second open end 29 which leads to the ventilator. The cylindrical configuration of the tubular member defines a longitudinal axis 30 through the center of the air flow sensor 22 in the direction of the respiratory air flow. The hollow, cylindrical tubular member of course provides a passage for the flow of air between the ventilator and patient. In the preferred embodiment, the air flow sensor 22 has on one end a slightly smaller diameter or cross section than the other end for connecting it to standardized ventilator tubing 20. The cylindrical configuration of the air flow sensor 22 preferably defines a conventional 15 mm ID/OD airway as required under ISO 5356-1. The nominal length of the sensor is preferably about 2.5 inches.

The air flow sensor 22 is a fixed orifice type sensor having a specified internal geometry which creates a resistance to the patient's inspired and expired air flows. The resistance produces a pressure differential between two longitudinally spaced apart air ports 31 and 33 in the air flow sensor 22. The measured pressure values are then used to calculate the air flow rate of the patient's respirations.

The internal geometry of the air flow sensor 22 is defined by the inner diameter of the cylindrical walls of the tubular member and also by a plurality of fixed internal vanes or fins 34, 35, 36 and 37 circumferentially spaced apart around the inside of the sensor walls. Each vane or fin is comprised of an aerodynamically curved or arcuate shaped surface extending along the inner surface of the cylindrical walls. The aerodynamic surfaces are elongated members oriented longitudinally along the inner surface of the sensor walls in a direction parallel to the longitudinal axis of the tube. The aerodynamic surfaces project inwardly from the walls toward the longitudinal axis 30 of the tube, but are not connected to each other.

Each fin may be generally described as a pair of partial spherical surfaces 38 and 39 joined together to define a common line of symmetry 40 which extends in a generally longitudinal direction through the air flow conduit. There are preferably four fins 34, 35, 36 and 37 within the tubular member with each fin spaced equidistantly approximately 90 degrees apart from the next adjacent fin.

As such, the internal geometry is comprised of first 34, second 35, third 36 and fourth 37 aerodynamically curved surfaces extending from the inner surface of the cylindrical walls of the air flow sensor 22 inwardly into the air passage. The first curved surface 34 extends from the inner wall of the tubular member a distance approximately equal to the radial distance between the wall of the housing and the longitudinal axis 30 of the tubular structure. The second 35, third 36 and fourth 37 curved surfaces extend into the passageway a distance which is less than the radial distance between the wall and longitudinal axis 30 of the air flow sensor 22. Therefore, there is a space separating each of the curved surfaces in the air flow sensor 22 from each other.

The first curved surface 34 in the air flow sensor 22 also has a first air port 31, second air port 32, and third air port 33. The three small air ports may alternatively be referred to as lumens in the sense that they are small bores in the side wall of the air flow sensor 22. Each air port or lumen extends radially from the exterior surface of the cylindrical walls of the air flow sensor 22 radially inwardly into the air passage. The first 31 and third air ports 33 are longitudinally spaced apart from each other and are used for measuring the pressure at each port, respectively. As the patient inhales and exhales, air of course flows through the air passage of the sensing device. The internal geometry of the sensor creates a small pressure drop as the air flows through the passage between the first and third air port 33. The difference in pressure between the first air port 31 and the third air port 33 is used to calculate the air flow rate.

Figure 7:
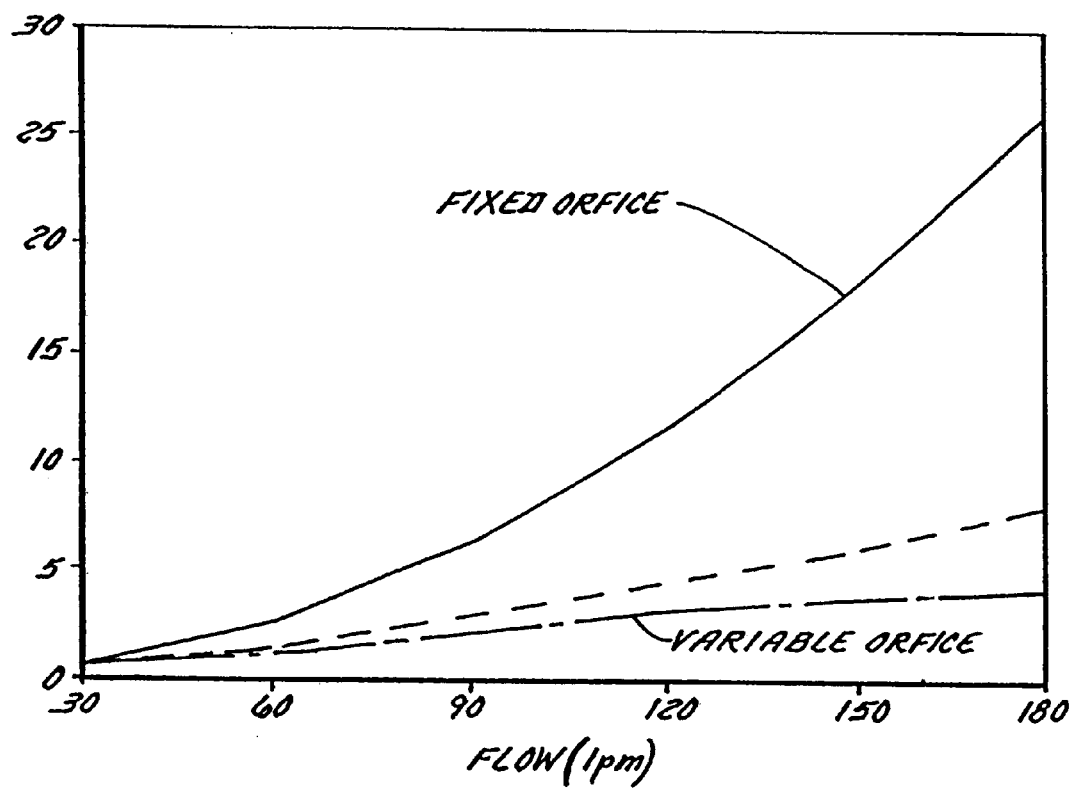
FIG. 7 is a graph representing the air flow rate versus pressure with the dashed line (middle line) representing the performance of the air flow sensor of the present invention as compared to a fixed orifice sensor such as the '633 device and to a variable orifice sensor such as the '621 device discussed above.
Figure 8:
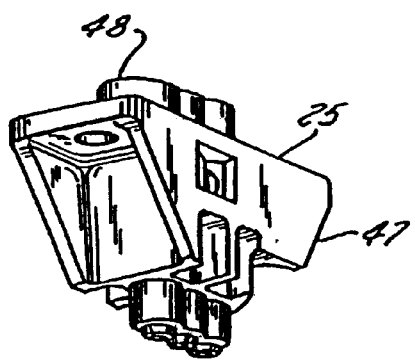
FIGS. 8 and 9 are perspective views of the tubing connector.
Figure 9:
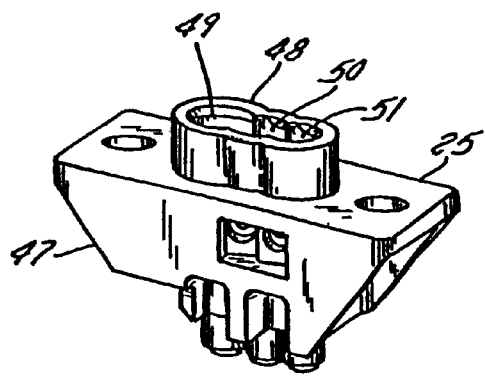
Figure 10:
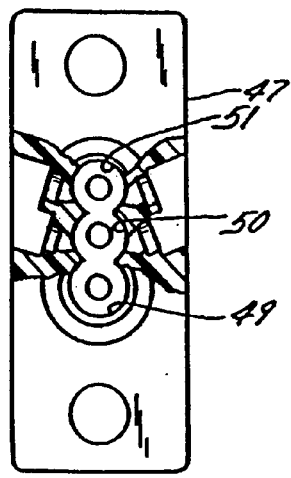
FIG. 10 is a partial sectional side view of the tubing connector.
Figure 11:
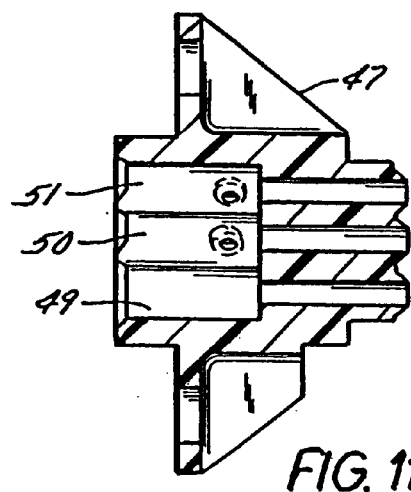
FIGS. 11 and 13 are cross-sectional views of the connectors.
Figure 12:
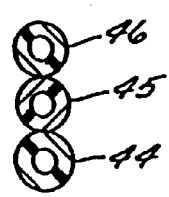
FIG. 12 is a cross-section view of the lumen tubing.
Figure 13:
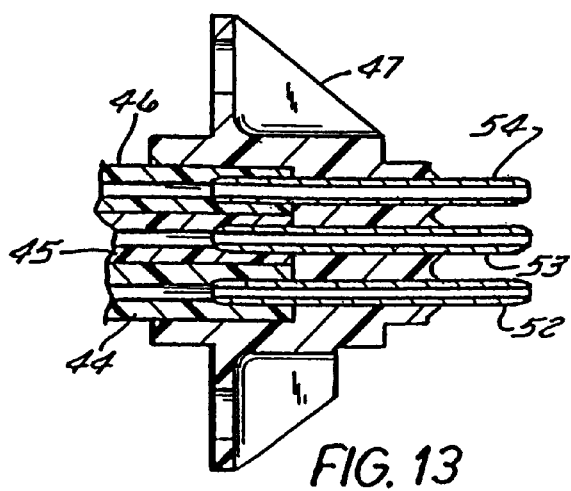
Figure 14:
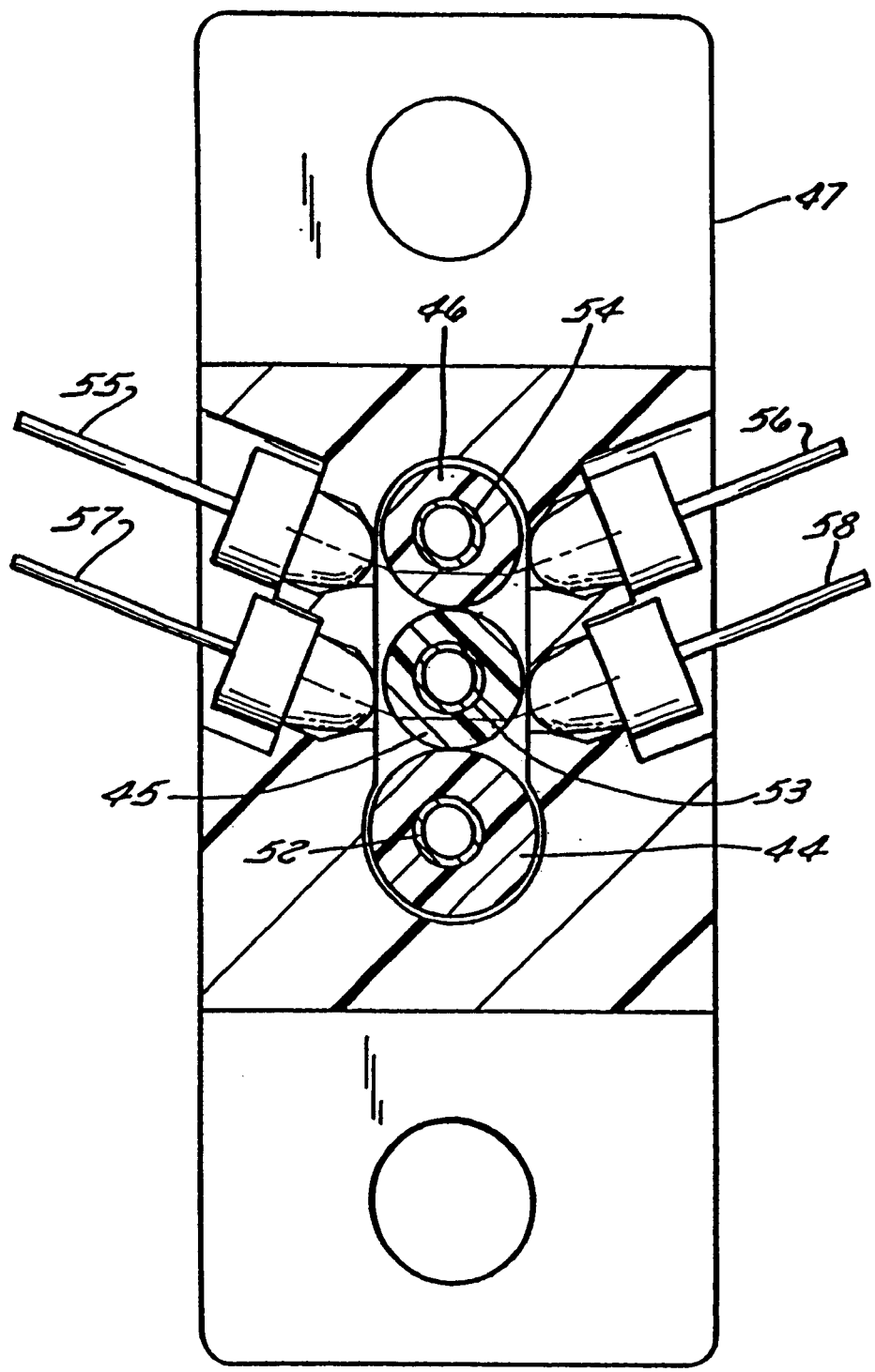
FIG. 14 is a cross-section view of the tubing connector showing the LED emitters and detectors and the manner in which light from the emitter is refracted by the lumen tubing and directed to the detector.
Figure 15:
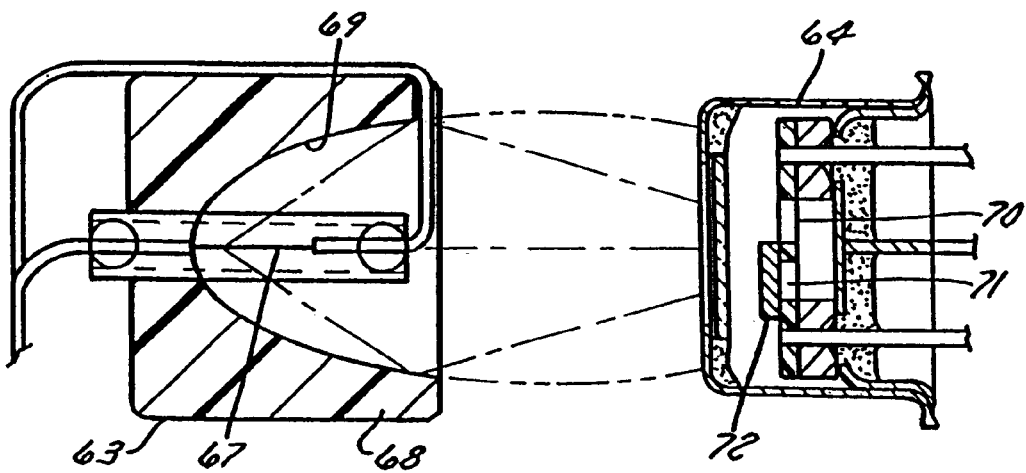
FIG. 15 shows the relative position of the infrared emitter and detector of the IR analyzer.
Figure 16:
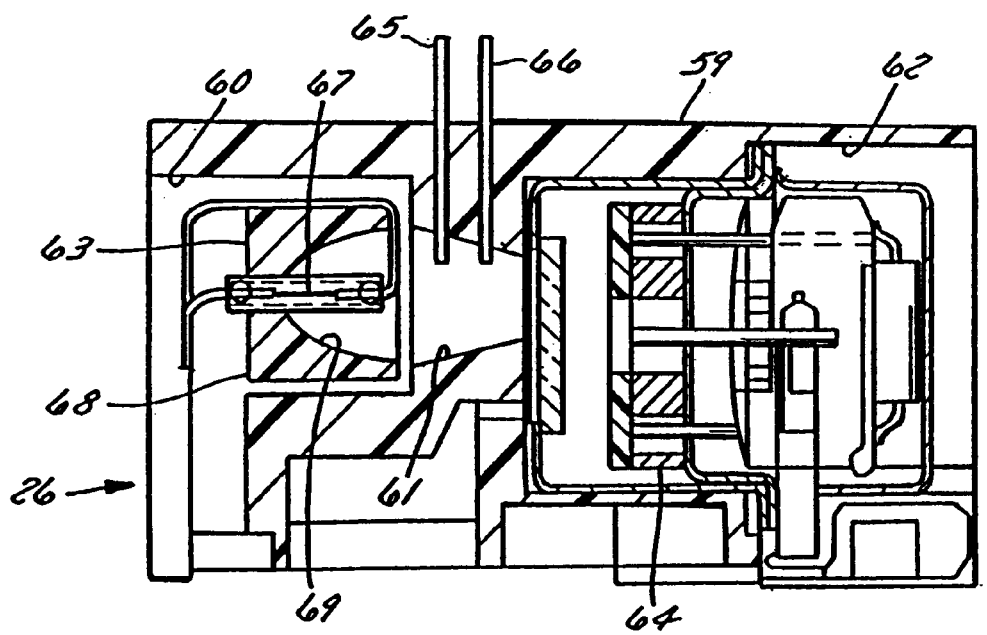
FIG. 16 is a cross-section view of the infrared gas analyzer.
Figure 17:
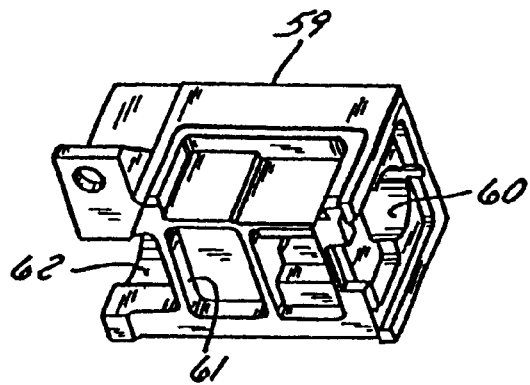
FIG. 17 is a perspective view of the infrared analyzer housing.
Figure 18:
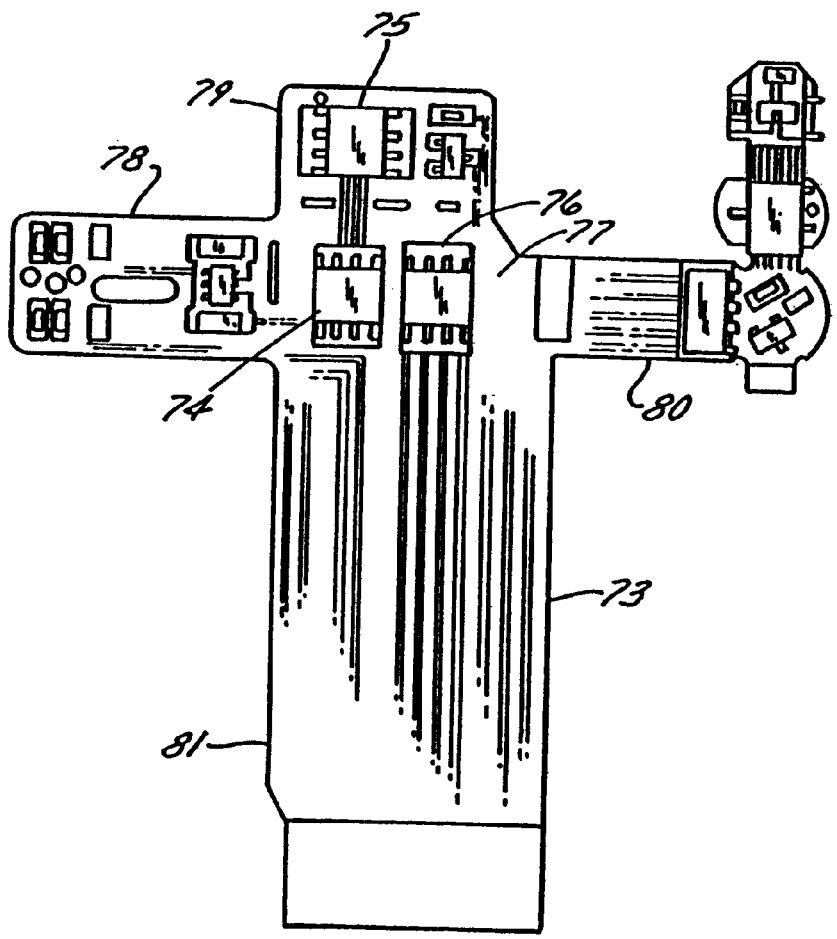
FIG. 18 is a top view of the flexible electronic circuit strip for the infrared gas analyzer.
Figure 19:
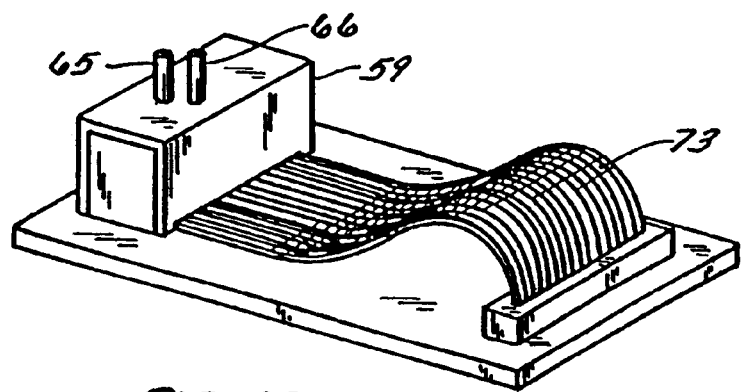
FIG. 19 is a perspective view of the replaceable infrared gas analyzer subassembly mounted to a circuit board.
Figure 20:
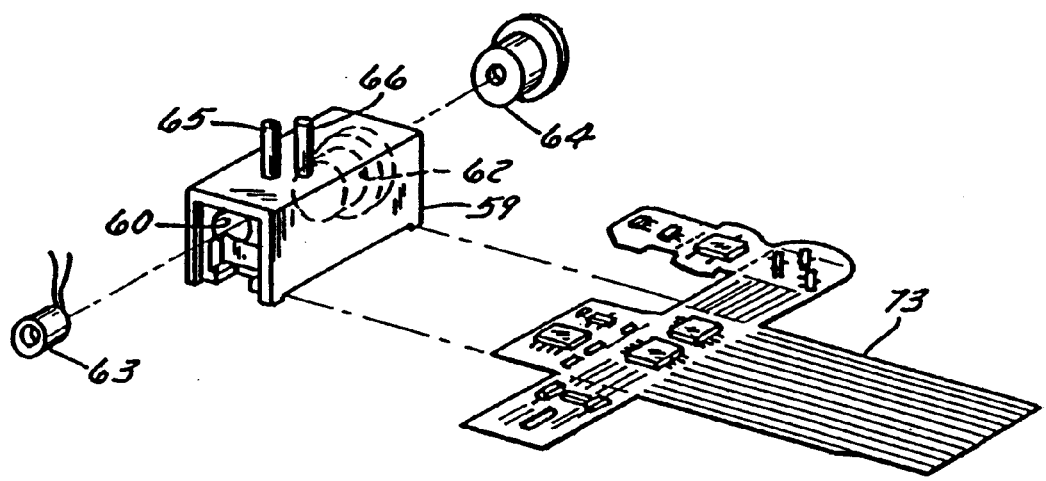
FIG. 20 is an exploded view of the infrared gas analyzer subassembly.

The air pressure in the first and third air ports is transmitted through the lumen tubing 23 to the analyzer. Within the analyzer module 24 is an electronic subassembly which converts the air pressure in the lumen tubing 23 into an electronic signal representative of the pressure difference between the first and third lumen tubes, and then through the use of a mathematical algorithm calculates the air flow rate. As mentioned, the novel internal geometry of the air flow sensor disclosed herein produces a highly desirable, nearly linear pressure versus air flow rate curve as reflected in the graph in FIG. 7.

Figure 21:
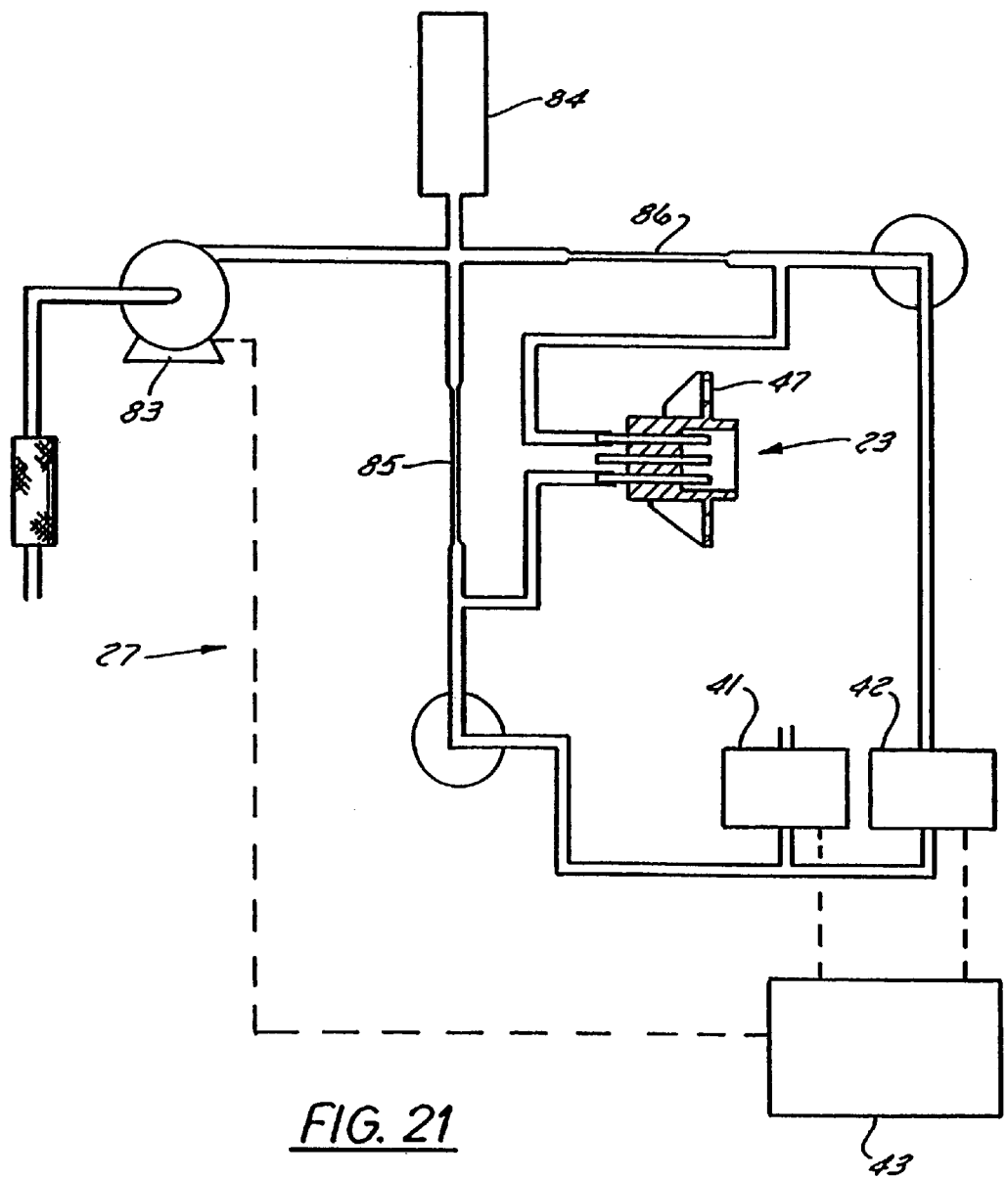
FIG. 21 is a pneumatic diagram of the continuous purge system.

Referring to FIG. 21, the pneumatic components for calculating the air flow rate in the analyzer module 24 include a pressure transducer 41, a pressure differential transducer 42, and an electronic microprocessor 43. The first air port 33 in the air flow sensor 22 is pneumatically connected through the connector 25 (discussed further below) to the pressure transducer 41 and to the pressure differential transducer 42. The third air port 33 in the air flow sensor 22 is also pneumatically connected through the connector 25 to the pressure differential transducer 42. The pressure transducer 41 obtains an absolute pressure reading of the patient's respiration and converts it to an electrical signal which is transmitted to the microprocessor 43. The pressure differential transducer 42 determines the difference in pressure between the first 31 and third air ports 33 in the air flow sensor 22 and converts it to an electrical signal which is likewise transmitted to the microprocessor 43. The microprocessor uses the signals obtained from the two transducers to calculate the patient's respiratory air flow rate.

The second air port 32 lies directly between the first and third air ports, and it is used for extracting a sample of the patient's respiratory gases for analysis, which is discussed further below.

The three air ports 31, 32 and 33 are preferably in the form of three small cylindrical recesses in the side wall of the air flow sensor 22. The recesses receive corresponding lumen tubing 44, 45 and 46 for connecting the air flow sensor 22 to the analyzer module 24. The diameter of the recess for the first air port 31 is slightly larger than the diameter of the second 32 and third air ports 33. For example, the diameter of the first cylindrical recess 31 is preferably about 0.1260 inches, while the diameter of the second 32 and third cylindrical recesses 33 are both preferably about 0.1050 inches.

The triple lumen tubing 23 is comprised of a first lumen tube 44, second lumen tube 45, and third lumen tube 46, which are inserted into the recesses which form the first air port 31, second air port 32, and third air port 33, respectively. The diameters of the three lumen tubes of course correspond to the diameters of the female recesses for the three air ports, respectively. That is, the outer diameter of the first lumen 44 is preferably about 0.1260 inches, while the outer diameters of the second 45 and third lumen tubes 46 are both preferably about 0.1050 inches. The internal diameters of all three lumen tubes are identical, preferably about 0.0550 inches. Of course, different specific dimensions may be used so long as they are used consistently as outlined above.

When the patient exhales the air obviously flows through the sensor 22 in one direction and when the patient inhales air flows in the opposite direction. It is therefore imperative that the first 31, second 32 and third air ports 33 be connected to the analyzer module 24 in the proper polarity so that the device records the inspired and expired air flows correctly. The different diameters of the recesses for the three air ports thereby discriminate in receiving the different sizes of lumen tubes in order to ensure the air flow sensor 22 is connected to the analyzer module properly.

The air flow sensor 22 of the present invention is capable of measuring respiratory air flow preferably in a flow range of about 1 to about 180 lpm (i.e., about 16 to about 3000 ml/s) with an accuracy of about +/−0.5%, or within about 0.5 lpm. The internal geometry described above adds an airway resistance of approximately only 2.0 cm $H_2O$ at 1 lps.

The air flow sensor 22 is a unitary plastic molded item which is inexpensive to manufacture. The internal geometry is defined by regular surfaces that are easily fabricated, especially from molded plastic. The sensor is of a one-piece construction which has no internal moving flaps or membranes. The pressure signals and gas samples are transmitted to the analyzer module through a conventional medical grade of polyvinyl chloride lumen tubing 23 which plugs directly into the novel connector 25 described further below. Accordingly, the air flow sensor 22 and lumen tubing 23 together provide a highly reliable, very accurate, inexpensive, disposable respiratory air flow measuring device.

2. Tubing Connector

Referring to FIGS. 8–14, the connector 25 is especially adapted to act as an interface between the analyzer module 24 and the air flow sensor 22. Specifically, the connector 22 provides a means for connecting the lumen tubes 44, 45 and 46 from the air flow sensor 22 to the analyzer module 24. It further provides a means for discriminating the proper polarity of the lumen tubes and a means for identifying one of several types of air flow sensors which can be used with the system.

The connector 25 is comprised of a connector housing 47 which is attached to the side of the analyzer module 24. The connector housing 47 includes a female socket 48 for receiving the triple lumen tubing 23 from the air flow sensor 22. The socket 48 is comprised of a first portion 49 for receiving the first lumen tube 44, a second portion 50 for receiving the second lumen tube 45, and a third portion 51 for receiving the third lumen tube 46. The first 49, second 50 and third portions 51 of the socket 48 are each substantially cylindrical in shape and each have a diameter corresponding to the diameters of the respective lumen tubes 44, 45 and 46.

Molded into the socket are three short stainless steel connector tubes which are also used for receiving the lumen tubes. Specifically, there is a first connector tube 52 located in the center of the first portion 49 of the socket 48 for receiving the first lumen tube 44, a second connector tube 53 located in the center of the second portion 50 of the socket 48 for receiving the second lumen tube 45, and a third connector tube 54 located in the center of the third portion 51 of the socket 48 for receiving the third lumen tube 46. The three metal connector tubes thereby provide three air passageways for connecting the three lumen tubes to the internal components of the analyzer module. The three metal connector tubes each have an outer diameter that is slightly larger than the internal diameter of the lumen tubes. For lumen tubes having an internal diameter of about 0.055 inches as mentioned above, the metal connector tubes preferably have an outer diameter of about 0.0575 inches, thereby making the outer diameter of the metal connector tubes about 0.0020 inches larger than the internal diameter of the lumen tubes.

As mentioned, the lumen tubing 23 is preferably made of polyvinyl chloride (PVC) which in this case is a somewhat flexible material. The lumen tubes preferably have a hardness Durometer of about 75 to 80, and preferably about 78. The metal connector tubes 52, 53 and 54 are of course dense, extremely rigid metallic members. The lumen tubes and connector tubes are sized such that, when one pushes the triple lumen tubing into the socket 48, the relatively softer PVC material compresses so that the lumen tubes slip over the slightly larger rigid connector tubes fairly easily. Once the tubing is in the socket, the PVC material, which is no longer being compressed by the user, attempts to expand back to its normal size and shape, but at this point the wall of the lumen tubing is compacted between the outer diameter of the metal connector tube and the inside wall of the socket. The compaction of the lumen tubes within the socket provides enough frictional force to hold it in place for normal usage. Consequently, the lumen tubing 23 fits fairly easily and snugly into the socket 48 and over the connect tubes, yet the lumen tubing may also be selectively disconnected from the module by yanking the tubing out of the socket. In this way, the air flow sensor 22 and lumen tubes 23 are detachable and disposable, and the analyzer module 24 is reusable by merely connecting a new air flow sensor to it.

The polarity that the air flow sensor 22 is attached to the connector 25 is of course established by the order of and by the different sizes of the three lumen tubes 44, 45 and 46. The socket 48 in the connector 25 for receiving the tubes is shaped to maintain the same polarity as the air flow sensor 22. In other words, the shape of the side walls of the socket 48 corresponds to the outer diameter of the three lumen tubes so that the lumen tubes 23 can be attached to the connector in only one way. Specifically, the diameter of the first portion 49 of the socket 48 is slightly larger than the diameters of the second 50 and third portions 51 of the socket. As a result, the first lumen tube 44 fits only into the first portion 49 of the socket 48, the second lumen tube 45 fits only into the second portion 50 of the socket 48, and the third lumen tube 46 fits only into the third portion 51 of the socket 48.

The connector 25 further includes two pairs of internal LED emitters and detectors 55, 56, 57 and 58 placed in lighting recesses positioned adjacent to the tubing socket 48. The emitter and detector pairs are not pointed directly at each other, but are instead angularly offset from each other so that when the tubing 23 is properly seated in the socket, light energy from the emitter is refracted by the tubing and thereby directed to impinge on the detector. When no tubing is present, light energy from the emitter is of course not refracted by the tubing and is merely directed into the side wall of the socket 48. Therefore, unless the tubing 23 is present and properly seated in the socket 48, the detector remains dark.

The first emitter and detector pair 55 and 56 are used in combination for the purpose of detecting the presence and proper seating of the lumen tubes 23 in the recess 48. The second emitter and detector pair 57 and 58 are used in combination for identification of one of several types of air flow sensors that can be used on the system. For instance, one type of air flow sensor may be especially designed for use on adult patients, and a second air flow sensor may be specially designed and adapted for use on pediatric patients. The lumen tubing 23, or at least the ends thereof, may be color coded for identifying and distinguishing between different types of air flow sensors. Coloring dye on the end of one of the lumen tubes will block the light energy emitted from one of the emitters from reaching the detector. Thus, activation of the first emitter and detector pair determines the presence and proper seating of the lumen tubing in the socket, which is assumed to have an air flow sensor on the other end of the tubing, and thereby activates the respiratory monitoring system. Activation (or non-activation, as the case may be) of the second emitter and detector pair identifies whether the air flow sensor is of the type used for adult patients or pediatric patients, which in turn activates the appropriate program for the particular type of patient being monitored.

The tubing connector 25 of the present invention thereby provides in a single plastic molded part all of the features necessary to ensure a positive connection and identification of the air flow sensor 22 to the monitoring electronics in the analyzer module 24. The connector design described above eliminates the need for a second male connector of the type typically found in prior art monitoring systems.

3. Infrared Gas Content Analyzer

As mentioned, the second or middle air port 32 in the air flow sensor 23 is used to extract a small sample of respiratory gases for analysis through the use of infrared spectroscopy. Such gas samples are of course transmitted from the air flow sensor 22 through the middle lumen tube 45 to the analyzer module 24. The analyzer module 24 contains an infrared gas content analyzer subassembly 26 for analyzing the content of specified respiratory gases, normally either carbon dioxide ($CO_2$) or nitrous oxide ($N_2O$). Referring to FIGS. 15–20, the infrared gas content analyzer subassembly 26 is comprised of a plastic molded analyzer housing 59. The IR analyzer housing 59 is divided essentially into three compartments, namely, a first compartment 60 for containing an infrared light source 63, a second compartment 61 comprising a gas chamber which the gas samples are passed through, and a third compartment 62 for continuing an infrared detector 64. The gas chamber 61 is of course between the infrared emitter chamber 60 and the detector chamber 62 and the gas chamber 61 includes an inlet 65 for introducing the gas sample into the chamber and an outlet 66 for exhausting such gases 65 from the chamber.

The infrared emitter 63 is comprised of a broad band, high efficiency infrared light source 67 assembled onto an emitter housing 68. The emitter housing 68 has a polished elliptical reflecting surface 69 for reflecting light from the light source 67 toward the detector 64 on the other side of the gas chamber. An ellipse of course has a central longitudinal axis, a first focal point and a second focal point. The light source 67 and the detector 64 are arranged in the housing 59 so that the light source 67 is located at the first focal point of the ellipse and the detector 64 is located at the second focal point of the ellipse so that a maximum amount of light energy from the source is reflected by the elliptical reflecting surface 69 toward the detector 64.

The infrared light source 67 is essentially comprised of an elongated filament having on each end an electrical connection. The filament is oriented so that it lies lengthwise along the central longitudinal axis with a central portion of the filament positioned at the focal point of the elliptical reflecting surface. The longitudinal orientation of the filament in this manner provides the greatest amount of light energy to become focused on the detector, thereby enhancing the reliability of the reading. Further, because the light energy is being used in the most efficient manner possible, the amount of light energy and therefore the amount of heat generated by burning the filament is minimized, as is the amount of time necessary to heat up the infrared light source to operational parameters.

The infrared detector 64 is actually a pair of detectors 70 and 71 connected in series, the detectors being sensitive to heat from the infrared source 67. The two detectors 70 and 71 are arranged in combination with a light filter 72 so that one detector 70 is subjected to only light passing through the filter 72, and the other detector 71 is altogether blocked from light from the infrared source 67. The light filter 72 may be comprised, in the case of $CO_2$ analysis, for example, from a thin sapphire window pane which passes through only a specific wavelength of infrared light which is naturally absorbed by $CO_2$. The light filter 72 consequently blocks all but the desired wavelength of light. Therefore, the light striking the one detector 70 is limited to the desired wavelength. The two detectors 70 and 71 are of course subjected to the same ambient temperature, pressure, humidity and so forth; the only difference between the two is the amount of infrared light striking the one detector. Moreover, the amount of light striking the one detector is a direct function of the amount of light energy which has been absorbed by the particular gas which is being analyzed. The two detectors 70 and 71 are therefore heated at different rates, which creates a small voltage between them which is in turn used to calibrate the amount of $CO_2$, or $N_2O$ as the case may be, in the gas sample.

Although the novel arrangement of the filament 67 disclosed above produces a longer lasting light source, infrared light sources are notoriously prone to burn out. The gas chamber 61 and infrared detector 64 are also notoriously prone to blockages which if that occurs obviously leads to incorrect results. The infrared gas analyzer 26 disclosed herein is therefore uniquely constructed as a replaceable subassembly.

Attached to the housing 59 is a flexible electronic circuit strip 73 which provides all of the necessary electronic components for the infrared analyzer, including electrical connections to the infrared light source 63, electrical connections to the detector 64, barometric pressure and temperature compensating components 74 and 75 and an EEPROM memory chip 76 for calibrating the sensor. The flexible electronic strip 73 is a somewhat cross-shaped member which has a central portion 77 attached to the bottom of the housing, a first flap 78 which folds over and is attached to a first side of the housing and at that point is also elastically connected to the light source 63 in the first compartment 60 of the housing 59, a second flap 79 which folds over and is attached to a second side of the housing, a third flap 80 which folds over and is attached to a third side of the housing and at that point is also electrically connected to the infrared light detector 64, and a fourth flap 81 which extends outwardly from the housing and terminates at an end which may be plugged into an electrical socket on a circuit board within the analyzer housing.

Molded into the housing of the infrared analyzer are two metal connector tubes, namely, a first tube 65 which provides an air inlet for inputting the gas sample extracted from the patient's respirations by the air sensor into the gas chamber 61 in the housing 59, and a second tube 66 which provides an air outlet for exhausting the sample from the gas chamber 61 into the atmosphere. The housing 59, further includes a means for fastening the housing to the circuit board, such as a threaded screw 82 or other equivalent device which will adequately secure the housing to the circuit board yet also facilitate easy, in-the-field replacement of the housing. Thus, all of the essential elements for an infrared gas analyzer, including the means to calibrate it in the field, are provided in one easily replaceable package.

4. Continuous Purge

The lumen tubes are purged by the introduction of a continuous low volume, low pressure air flow into the tubes. The continuous purge is produced by a pneumatic subassembly 27 contained within the housing of the analyzer module 24. As mentioned, a pneumatic diagram of the pneumatic subassembly 27 for the continuous purge is illustrated in FIG. 21. A continuous purge of the air flow sensor lumen tubes 31 and 33 provides two unique advantages in comparison to the periodic purge found in the prior art. First, a continuous purge reduces the depth of compressed gas coming into the sensor tubing. Secondly, the exit of the purging gas from the lumen tubing into the air flow sensor 22 prevents or at least inhibits particulate $H_2O$ droplets from forming around the air orifice. This means that when the pressure surge from the compressible volume effect happens, there will be less chance of large droplets being drawn up into the tubing. Consequently, a continuous purge of the air flow sensor lumen tubes prevents blockage from occurring in the tubes in the first instance, and further permits a continuous monitoring of the patient.

The continuous purge approach of course requires balancing the purging air flow. In other words, the values and pressure of the purging air flow must be equal into both sensor tubes 31 and 33. If the purge flow is not equal, errors will be introduced by the purge system into the respiratory measurement calculations.

Referring again to FIG. 21, the pneumatic components of the purge system include an air pump 83, an air pressure reservoir 84, and two pneumatic resisters 85 and 86. As mentioned above, pressure readings from the air flow sensor 22 are pneumatically transmitted through the first lumen tube 31 and third lumen tube 33 to the analyzer module 24. (The second lumen tube 32, which is the middle tube and is used for transmitting the gas sample to the infrared gas analyzer, is not part of the purge system.) The air pump 83 and reservoir 84 provide a single source of pressurized purging air for both the first 31 and third lumen tubes 33.

The air purge 83 and pressure reservoir 84 are pneumatically connected through the first pneumatic resisters 85 to the first lumen tube 31, and connected through the second pneumatic resister 86 to the third lumen tube 33. The resisters 85 and 86 serve two essential functions. First, the resisters isolate the first and third lumen tubes from each other. The isolation factor permits the use of a single pump and reservoir for both pressure lines, which simplifies the pump control. If the differential pressure lumens 31 and 33 were instead tied together through a single reservoir, without the resisters, the two pressure lines would automatically null each other out and no flow measurement could be made. Second, the pneumatic resisters 85 and 86 provide a means for bleeding a small volume of low pressure air from the reservoir 84 into the lumen tubes 31 and 33. The resisters 85 and 86 are preferably comprised of a bundle of teflon coated conductors encapsulated in polyvinyl chloride coating, e.g., 19 gauge multi-strand electrical wire. The insulating coating on the wire acts as a pneumatic conduit, and the bundle of wires within it severely restricts the flow of air through the conductor. Thus, a common electrical wire effectively acts as a pneumatic resister which controls the amount of purge air introduced into the system.

Because the amount of resistance provided by the pneumatic resisters 85 and 86, is very high compared to the air pressure in the reservoir 84, and because the length of the first 85 and second pneumatic resister 86 are substantially the same, the purge system introduces the purging air into both the first 31 and third lumens 33 at substantially the same low volume and at substantially the same low pressure. This is important because if the lumens were purged at different volumes or pressures, then an error would be introduced into the air flow rate calculations, which is of course undesirable.

Of course, specific details of the invention as disclosed herein are not to be interpreted as limiting the scope of the invention, but merely provides a basis for the claims and for teaching one skilled in the art to variously practice and construct the present invention in any appropriate manner. Changes may be made in the details of the construction of the respiratory measurement system disclosed herein, and in the particular components of the system, without departing from the spirit of the invention, especially as defined in the following claims.

What is claimed is:

1. An analyzer module adapted for use with a patient respiratory system that includes a conduit through which the patient inhales and exhales a gas, the module comprising:
    a) a first tube adapted to be connected to the conduit;
    b) a second tube adapted to be connected to the conduit and spaced from the first tube;
    c) a third tube operably connected to the first and second tubes opposite the conduit;
    d) a source of pressurized air connected to the third tube opposite the first and second tubes; and
    e) a controller operably connected to the source of pressurized air, wherein the controller is used to control the flow of pressurized air in order to provide a constant purging airflow to the first and second tubes.

2. The analyzer module of claim 1, wherein the third tube includes a pair of resistors located between the air source and the first and second tubes, respectively.

3. The analyzer module of claim 2 wherein the resistors each comprise a plurality of coated conductors encapsulated in a flexible material.

4. The analyzer module of claim 3 wherein the flexible material is plastic.

5. The analyzer module of claim 4 wherein the flexible material is polyvinyl chloride.

6. The analyzer module of claim 2 wherein the conductors are formed of metal.

7. The analyzer module of claim 2 wherein the conductors are coated with Teflon.

8. The analyzer module of claim 1 further comprising a pressurized air reservoir attached to the third tube between the resistors and the pressurized air source.

9. An analyzer module adapted for use with a patient respiratory system that includes a conduit through which the patient inhales and exhales a gas, the module comprising:
    a) a first tube adapted to be connected to the conduit;
    b) a second tube adapted to be connected to the conduit and spaced from the first tube;
    c) a pressure transducer connected to the first tube opposite the conduit;
    d) a differential pressure transducer connected to the second tube opposite the conduit and to the first tube opposite the conduit;
    e) a microprocessor operably connected to the pressure transducer and a differential pressure transducer, the microprocessor capable of calculating an airflow rate based on signals generated by the pressure transducer and the differential pressure transducer; and
    f) a continuous purge mechanism connected to the analyzer module, the mechanism including a low pressure gas source, and a third tube connected between the gas source and the first tube and the second tube, the third tube including a pair of resistors between the gas source and the first and second tube.

10. The analyzer module of claim 9 wherein the pressure transducer and the differential pressure transducer are connected to the first tube in parallel.

11. The analyzer module of claim 9 wherein the first tube is disposed opposite the pressure transducer and differential pressure transducer within a housing adapted to be connected to the conduit.

12. The analyzer module of claim 11 wherein the second tube is disposed opposite the differential pressure transducer within the housing.

13. The analyzer module of claim 12 wherein the first and second tubes provide upstream and downstream gas pressures, respectively, of the gas flowing through the conduit.

14. The analyzer module of claim 9 wherein the mechanism further includes a low pressure gas reservoir connected to the third tube between the gas source and the resistors.

15. A method of purging airflow lines of blockages in a patient respiratory system airflow analyzer, the method comprising the steps of:

1) providing an analyzer including a connector adapted to be connected to a breathing conduit for the respiratory system, the connector having a first tube operably connected to a source of pressurized air, and a second tube spaced from the first tube and operably connected to the source of pressurized air, and 2) supplying a constant flow of pressurized air from the source through the first and second tube to purge the first and second tubes of any blockages.

16. The method of claim 15 wherein the first and second tubes each include a resistor utilized to control the flow of air through the first and second tubes, respectively.

17. The method of claim 15 wherein the pressurized air is supplied at low pressure.

18. The method 15 wherein the source of pressurized air includes an air pump.

19. The method of claim 18 wherein the airflow analyzer further includes a differential pressure transducer connected to the first and second tubes, and a controller operably connected to the air pump and to the pressure differential transducer; and wherein the step of supplying the pressurized air comprises the steps of:

1) measuring a pressure differential between the first and second tubes in the pressure differential transducer;

2) outputting a signal representing the measured pressure differential to the controller; and 3) altering the flow of pressurized air from the air pump.

20. In a respiratory measurement system, a pneumatic subassembly for purging with a continuous stream of low pressure and low volume air lumen tubing connecting an air flow rate sensor to an analyzer module, the lumen tubing including at least a first lumen tube and a second lumen tube, said pneumatic subassembly comprising:

a) an air pump and an air reservoir for producing a volume of relatively high pressure air;

b) a first pneumatic resister pneumatically connected to the air pump and air reservoir and to the first lumen tube; and c) a second pneumatic resister pneumatically connected to the air pump and air reservoir and to the second lumen tube;

whereby a small volume of air migrates from the volume of relatively high pressure air through the first and second resisters and into the lumen tubing.

* * * * *